United States Patent [19]

Mick

[11] Patent Number: 5,117,835
[45] Date of Patent: Jun. 2, 1992

[54] METHOD AND APPARATUS FOR THE MEASUREMENT OF INTRACRANIAL PRESSURE

[76] Inventor: Edwin C. Mick, 3 Cole Rd., Chester, N.H. 03036

[21] Appl. No.: 752,870

[22] Filed: Aug. 30, 1991

Related U.S. Application Data

[60] Division of Ser. No. 738,230, Jul. 30, 1991, which is a continuation-in-part of Ser. No. 560,162, Jul. 31, 1990.

[51] Int. Cl.$^5$ ............................................. A61B 5/00
[52] U.S. Cl. ..................................... 128/748; 128/774
[58] Field of Search ...................... 128/748, 774, 782

[56] References Cited

PUBLICATIONS

Robert Coleman "Comparison of Microphone and Neck Mounted Accelerometer" Invited Paper, 16th Symposium, Core of the Professional Voice, Lincoln Center, New York, Jun. 1987.

Noom Gavriely, "Spectral Characteristics of Normal Breath Sounds," American Physiology Society, 1981.

Semmlow et al., "A Noninvasive Approach to Intracranial Pressure Monitoring," Journal of Clinical Engineering, Jan.-Mar. 1982.

*Primary Examiner*—Francis Jaworski
*Assistant Examiner*—Scott R. Akers
*Attorney, Agent, or Firm*—Hayes, Soloway, Hennessey & Hage

[57] ABSTRACT

A method and apparatus for non-invasively measuring changes in intracranial pressure (ICP) in a patient's skull which allow trends in such pressure to diagnosed over time. A method performed, or an apparatus made in accordance with the instant invention comprises a generation of a predetermined vibration signal which is applied to a first location on a skull, detecting an output vibration from another location on the skull, storing data characteristic of the two signals, repeating the above-mentioned steps over time, and analyzing the data to diagnose changes in ICP over time.

18 Claims, 5 Drawing Sheets

METHOD AND APPARATUS FOR THE MEASUREMENT OF INTRACRANIAL PRESSURE

This is a division of copending application Ser. No. 07/738,230 filed Jul. 30, 1991, which is, in turn, a continuation-in-part of application Ser. No. 07/560,162 filed Jul. 31, 1990.

BACKGROUND OF THE INVENTION

1. Field of the Invention

The present invention relates generally to the measurement of intracranial pressure. More specifically, this invention relates to the provision of an improved method and apparatus for the non-invasive measurement of changes in intracranial pressure.

2. Brief Description of the Prior Art

Measurement of intracranial pressure (ICP) has become a routine neurosurgical procedure used in monitoring patients with conditions such as head injury, intracranial infection, hemorrhage, and hydrocephalus.

Generally when ICP reaches 20 mm Hg it becomes a concern and when it reaches 25 mm Hg for more than 2 minutes it is considered life threatening. Normal ICP is considered to be 0-4 mm Hg.

There are a number of prior references on the measurement of fluid pressures within the body cavity. The applicable work known to applicant is set forth in the following references:

Murr, U.S. Pat. No. 3,853,117—fluid pressure within a body cavity is measured with the use of a sonic transponder implanted inside the body cavity, e.g., the cranium. A sound signal is sent to the transponder to emit a resonance signal which is received at an external detector. The method is based on the principle that the skull and the cranial fluid are good sound conductors and that there are no intervening structures to attenuate the input or output signals. The implanted transponder has a diaphragm which serves as a mechanically resonant structure. This technique has major drawbacks, however. It involves invasive methods which introduce significant risks due to the possibility of cerebral infections. Furthermore, the measurement of a sound signal by an external detector affects deleteriously the measured sound's signal to noise ratio due to background noise present in the environment and signal strength attenuation inherent in the use of external detectors to receive sound signals. Lastly, the characteristics of the measured sound (accoustic signal) signal are only indirectly related to changes in ICP and thus may give rise to inaccurate results.

Pratt, U.S. Pat. No. 4,361,154—describes a method of determining bone strength by measuring the relative speed of travel of sound through the bone. The method has particular application in determining the bone strength of a race horse's legs. The method is based on the principle that microcrushing and microfracturing which occur in bone over time in the process of absorbing shock results in a decrease in sound velocity measured across a section of the bone. Since the elastic modulus of bone is known to decrease as it weakens, there is a relationship between bone strength and rate of travel of acoustic energy through the bone. This patent, however, does not appreciate the measurement of ICP.

Rosenfeld, et al., U.S. Pat. No. 4,564,022—involves a method of non-invasively estimating ICP whereby electrical brain activity is generated by a stimulus. In particular, the patient's observance of a flashing light results in visual stimulation which causes visual evoked potentials signalled from the brain. These visual evoked potentials are measurable and their characteristics are well-defined in both children and adults. An accurate estimate of the subject's ICP can be made by measuring the latency of the second negative-going wave of the visual evoked potential. The method used to arrive at this estimate, however, is based upon the measurement of characteristics which are secondarily related to ICP. This may give results which are less accurate than those which may be obtained by measuring characteristics which are primarily related to ICP, such as vibration frequency characteristics.

Cosman, U.S. Pat. No. 4,676,255—this disclosure is a continuation-in-part of a patent relating to measuring ICP by using known pressure applied to the scalp over an implanted sensor. This particular patent focuses on measurement of negative ICP. Unfortunately, the problems which are inherent in the use of implanted (invasive) sensors are also present in this system.

Sackner, U.S. Pat. No. 4,860,766—provides a non-invasive method of monitoring intrapleural pressure of a newborn. The method is based on the principle that the cranial bones of a newborn move relative to each other during respiration as a result of a pressure wave transmitted from the pleural space through the cerebrospinal fluid and veins to the cranial cavity. The movements of the cranial bones are detected and monitored and the waveform produced directly relates to intrapleural pressure. This patent, however, does not offer any teaching that would allow one skilled in the art to measure ICP.

U.S. Pat. No. 1058-556-A—this Soviet patent describes a non-invasive method of measuring ICP whereby an ultrasound sensor is positioned on one side of the front of the cranium and a pulsing signal is sent through the cranium to the occipital wall of the skull and back. The reflected ultrasound signal is recorded and ICP is determined thereby based on a set of formulas relating to amplitude of echopulsation within the cranium. This method uses sound and, therefore, the problems present in the measurement of ICP using sound (for example, a poor signal to noise ratio) are also inherent in this method.

Devine, III, et al., IBM Technical Disclosure Bulletin—describes the measurement of internal pressure in a closed chamber within a living body whereby externally applied mechanical vibration is used to induce a differential Doppler by which internal pressure can be determined. The method is geared to the measurement of ventricular pressure in the heart. The frequency, amplitude and phase of the induced vibration are known, and the reflected ultrasonic energy is detected by a receiver. This technique uses sound detection and therefore in no way overcomes the difficulties, detailed previously, associated with the use of sound to measure pressure.

Kasuga, et al., "Transmission Characteristics of Pulse Waves in the Intracranial Cavity of Dogs," Journal of Neurosurgery, Vol. 66, Jun. 1987, pp. 907-914—discusses an attempt to mathematically model the intracranial pressure pulse wave transmission transfer function using the common carotid artery (randomized by using a cardiac pacemaker) as an input signal and the epidural pressure pulse wave as the output signal. The transfer function was estimated numerically from the autocorrelation function of the input signal and the cross-correlation function of the input and output signals by the least squares method. The results suggested that the lower frequencies of the pulse wave were suppressed during transmission through the intracranial cavity and that resonance was evident in the intracranial cavity under normal conditions. ICP could then be calculated using the transfer function and a known input signal. The technique used, however, has significant drawbacks. The greatest drawback is that the technique is invasive and thus involves the risk of intracranial infection. Furthermore, the technique is difficult to use, requires surgery, involves the dangers inherent in use of cardiac pacemakers, and presently is difficult to use in a clinical environment.

Kosteljanetz, et al., "Clinical Evaluation of a Simple Epidural Pressure Sensor," Acta Neurochirurgica, Vol. 83, 1986, pp. 108-111—This reference discusses the evaluation of Plastimed® epidural pressure (EPD) sensor in a number of patients suffering from head injury. The EPD sensor, a plastic cup 10 mm in diameter, was placed into a burrhole and two plastic tubes, one longer than the other, were connected to the cup. A pressure transducer was connected to the longer of the two tubes and the shorter tube was connected to saline reservoir via a stopcock. A conventional intraventricular pressure sensor (IVP) was situated next to the EPD sensor cup and recorded pressure continuously. The ICP values obtained from the IVP sensor were compared to those obtained from the EPD sensor. The comparison indicated that the EPD sensor gave inaccurate ICP readings. In addition to this drawback, the EPD system is invasive and requires careful alignment of the cup to the burrhole in order to obtain reasonable results. Furthermore, this method is subject to sudden sensor failure.

Takizawa, et al., "Spectral Analysis of the CSF Pulse Wave at Different Locations in the Craniospinal Axis," Journal of Neurology, Neurosurgery, and Psychiatry, Vol. 49, 1986, pp. 1135-1141—discusses a study intended to determine the change in frequency spectrum of the cerebrospinal fluid (CSF) pulse waveform, the amplitude transfer function from blood pressure to the CSF pulse and the conduction of each component of the CSF pulse through the CSF space under normal and abnormal conditions produced by saline infusion into the CSF space (thus elevating the pressure within the CSF space). Pressure transducers were positioned halfway between the tip of the dorsal spine and the sternum. CSF pulse and blood pressure under normal and artificially high CSF pressures were recorded at various sites. Several drawbacks are present in this method of pressure measurement. The method is invasive. Furthermore, the use of blood pressure as the input signal, with its discontinuous pressure values in between heart beats, can result in errors in the calculation of fluid pressure, since the transfer function obtained will be discrete rather than continuous.

Semmlow and Fisher, "A Noninvasive Approach To Intracranial Pressure Monitoring," Journal of Clinical Engineering, Vol. 7, March 1982, pp. 73-78—This reference discusses measurement of ICP by measuring the acoustical transmission properties of a skull under pressure. An impulse-like stimulus was applied to skulls suffering from various levels of elevated ICP. A piezo-electric acoustic pickup was used to monitor the acoustic response, resulting from the impulse stimulus, transmitted through the skull. Based on this monitored acoustic response, a second-order system response was modelled. Damping factor, a characteristic of a second-order system, was found to be indicative of elevated ICP. This method of ICP measurement, however, is subject to several problems. Acoustic transmission measurements, as previously mentioned, have poor signal to noise ratios. Furthermore, ICP measurements are derived, using this method, not from direct measurements but rather from artificial and often times inaccurate mathematical system model characteristics. This may lead to largely inaccurate ICP measurements.

Accordingly, the present invention generally has as its objective the provision of both a method and an apparatus for the measurement of ICP which overcomes the above-mentioned problems in the prior art. More specifically, the present invention has as an objective the provision of a method and an apparatus for the measurement of ICP which eliminates the risks of cerebral infections.

It is a further objective of the present invention to provide a method and an apparatus for the measurement of ICP which is not subject to large measurement errors due to poor signal to noise ratios of the measured signal.

It is a further objective of the present invention to provide a method and an apparatus that measure characteristics primarily related to ICP.

SUMMARY OF THE INVENTION

The method of the present invention measures changes in the ICP of a human being or animal non-invasively (without penetrating the skull).

The method is based on the principal of physics which states that the dynamic vibration characteristics and behavior, natural frequency, mechanical impedance, coherence characteristics, and frequency response spectrum of a material (bone in this case) will change in relation to the stress applied to the elastic material.

ICP generates within the patient's skull a stress in the form an internal pressure directed to the skull bone. As the ICP varies so does the stress in the skull bone which behaves as a curved elastic plate.

It has been found, therefore, that the changes in natural frequency and frequency response spectrum of the skull bone are indicative of changes in the stress acting on the skull bone and thus, indicative of changes in ICP. These changes in natural frequency and frequency response spectrum can be measured by application of a mechanical forced oscillation stimulus (such as a vibration exciter transducer or impact hammer) which creates a mechanical wave transmission through the bone material non-invasively. The frequency response spectrum is detected by a sensor (such as an accelerometer, velocity sensor, or displacement sensor) and is analyzed and compared to the exciting spectrum by an analyzer, such as a spectrum analyzer, a dynamic signal analyzer, or network analyzer. Thus, by comparing the spectral response data obtained from the application of a given stimulus at different times, the present invention allows one to recognize ICP trends over time. In several embodiments of the present invention, the stimulus is generated and applied and the response is detected by the same device and at the same location on a patient's skull; by an impact exciter transducer, for example. However, other embodiments of present invention, generate and apply the input signal at one location on a patient's skull and measure the resultant output vibration at different place on a patient's skull. By measuring the frequency response spectrum at a point on the skull which is not effected by ICP (at locations such as, the temporal, sphenoid, lower portions of the lower occipital, lower parietal, or lower frontal bones), a baseline measurement or normal ICP pressure measurement can be obtained. This baseline measurement may then be used to measure changes in ICP from what may be considered to be a patient's normal ICP. Baseline ICP may also be obtained by measuring the frequency response spectrum of a normal patient (one without elevated ICP).

As can be readily seen, the method of the present invention offers significant advantages over the prior art. First, non-invasive measurement of ICP eliminates the risk of cerebral infections inherent in invasive methods. Furthermore, the present invention measures the characteristics of mechanical vibrations and not sound. This results in a much more favorable signal to noise ratio than in the prior art acoustic methods and therefore, more accurate results. Additionally, the present invention measures characteristics directly associated with ICP and not characteristics which are only secondarily related to ICP. This also increases the accuracy of pressure measurement results.

BRIEF DESCRIPTION OF THE DRAWINGS

The basic ICP measurement system is shown in the attached drawing wherein:

FIG. 5 and 6 being plotted from the data shown on FIG. 3.

DETAILED DESCRIPTION OF THE INVENTION

Discussion of Underlying Theory

The skull can be considered as an elastic plate in the form of a sphere, and therefore, the vibration pattern of the skull approximates the vibration pattern of a spherical elastic shell. (Reference 1. von Bekesy, G.: J. Acoust. Soc. Amer., 20:749 (1948)(Reference 2. Franke, E. K.: USAF, WADC Tech. Pept. 54-24, 1954)(Reference 3. Harris, Cyril: "Shock & Vibration Handbook", ch 44, pg 17, 3rd Ed., McGraw Hill, 1988). The calculated value of elasticity of the skull, from the observed resonances, is $1.4 \times 10^{10}$ dynes/$cm^2$. The Fundamental resonant frequency for the skull is between 300 and 400 Hz and resonances for the higher modes around 600 to 900 Hz. Because of its elasticity, it has been found that changes in the natural frequency and the output frequency response spectrum of the skull bone under a pressure load can be measured in the following way.

Figure 1:
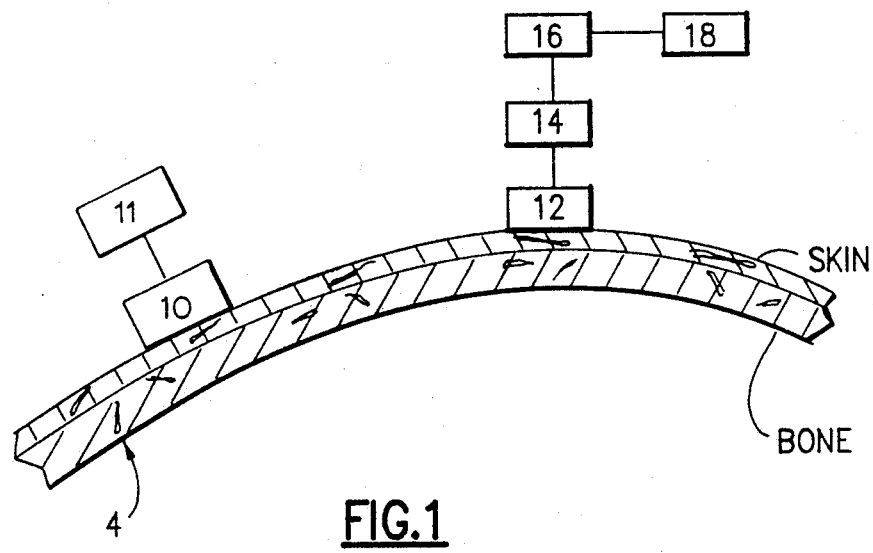
FIG. 1 is a Mechanical Schematic block diagram of a human skull showing the general position of exciter and sensing transducers and a generator and analyzing apparatus.

Turning to FIG. 1, a mechanical exciter transducer (10) is placed in contact with the outside of the skull (4) non invasively. The exciter transducer creates a mechanical vibratory wave and/or shock wave transmission laterally through the bone material. This input vibratory and/or shock wave signal (hereinafter referred to as an exciting stimulus) applied to the skull may take the form of time varying sinusoidal, periodic, phase coherent, complex, shock, or random functions. (Reference 5. Harris, Cyril: "Shock & Vibration Handbook", ch 22, pg 4. 3rd Ed., McGraw Hill, 1988). Moreover, the input signal may also take the form of continuous sum sinusoids, broad band random, or narrow band random pattern functions. (Reference 6. Harris, Cyril: "Shock & Vibration Handbook", ch 22, pg 2. 3rd Ed., McGraw Hill, 1988) Special types of shock input signals may also be used, such as, impulse, step, half sine, decaying sinusoid, and complex functions. (Reference 7. Harris, Cyril: "Shock & Vibration Handbook", ch 23, pg 2:ch 32, pg 6. 3rd Ed., McGraw Hill, 1988)

With the application of an exciting stimulus to the skull, analysis of the frequency response spectrum sensed by the detecting transducer (12) is made. One such analysis technique is the Fourier spectrum description of the shock and/or vibration stimulus acting through a transmission medium. The Fourier analysis may be applied to a linear system when properties of a structure on which a shock or vibration act may be modelled as a function of frequency. Such properties are mathematically modelled by the transfer function in which important characteristics of the medium, through which the exciting stimulus acts, may include. mechanical impedance, mobility, transmissibility.

The Fourier analysis, therefore, may be applied in evaluating the effect of a load upon a shock or vibration source. A source of shock generally consists of a means of shock excitation and a resilient structure through which the excitation is transmitted to the skull. The character of the shock or vibration transferred through the medium is influenced by the nature of the load being driven. The characteristics of the source and load may be defined in terms of mechanical impedance or mobility.

Periodic vibration functions represented by Fourier transform series consist of a sum of sine waves whose frequencies are all multiples of a fundamental harmonic frequency; furthermore, each of the terms have varying amplitude coefficients and phase angles.

The amplitude and phase data are plotted as a frequency domain-plot known as line spectrum or a discrete frequency spectrum (vertical lines) or power spectral density (vertical line peaks connected). The resulting plots directly indicate shifts in frequency spectral response due to changes in ICP. Therefore, trends in ICP over time may be observed using the present invention.

In order to obtain a baseline or normal ICP value, a further understanding of the theory underlying the present invention is necessary. (Of course, the following discussion is only meant to show some of the methods that have been found to measure baseline or normal ICP values and in no way is meant to limit the means and/or methods available to find such values. Other variations and response characteristics may be used to find such values.)

A skull bone which is exposed to changes in load or ICP may be modelled by a circular plate with a fixed circumferential edge. This theoretical modelling gives rise to the following mathematical expression for the change in natural frequency of a circular plate with a built in circumferential edge supporting a variable load at the center, which is: (vibr Hnbk pg 42-24)

$$Wn = \frac{\frac{t}{R^2}\sqrt{\frac{E}{\mu}}}{\sqrt{\frac{1}{N^2 p}+\left(\frac{\pi}{n_p}\right)\frac{M_L}{\mu t(\pi R^2)}}}$$

Where Constants
t = thickness of skull bone
R = radius of plate
E = Youngs modulus (lb/in$^2$)
$\mu$ = mass density of skull bone (lb-sec$^2$/in)
$n_p$ = constant based on material Poissons ratio
$N_p$ = constant based on mechanical constraint on perimeter of plate
$M_L$ = concentrated load at plate center which represents ICP.

The constants t and R are constant for a given patient. They will vary however from patient to patient. The radius of the plate, representing the skull, is measurable with a caliper or ruler.

The thickness of the plate (skull bone) is measurable by CAT (computer aided tomography) scan. Young's modulus is obtainable through demographic studies. The fundamental harmonic frequency, Wn, may be obtained experimentally for a given subject by observing the Fourier output frequency response spectrum for a given patient in a normal condition (that is, not exhibiting symptoms of abnormal ICP). The above equation may then be solved to obtain a given patient's normal ICP.

Two other methods for obtaining a normal or zero pressure ICP baseline measurement for a specific patient are presently described. For a patient with a pre-existing condition, as Hydrocephalus, periodic ICP measurements would be taken throughout the patient's past during conditions of normal pressure to establish a baseline analysis for reference should an emergency condition arise.

A baseline normal pressure could also be established by taking a spectral response measurement at a skull location not affected by ICP. One such location is at the temporal bone.

DISCUSSION OF PREFERRED EMBODIMENT

Figure 7:
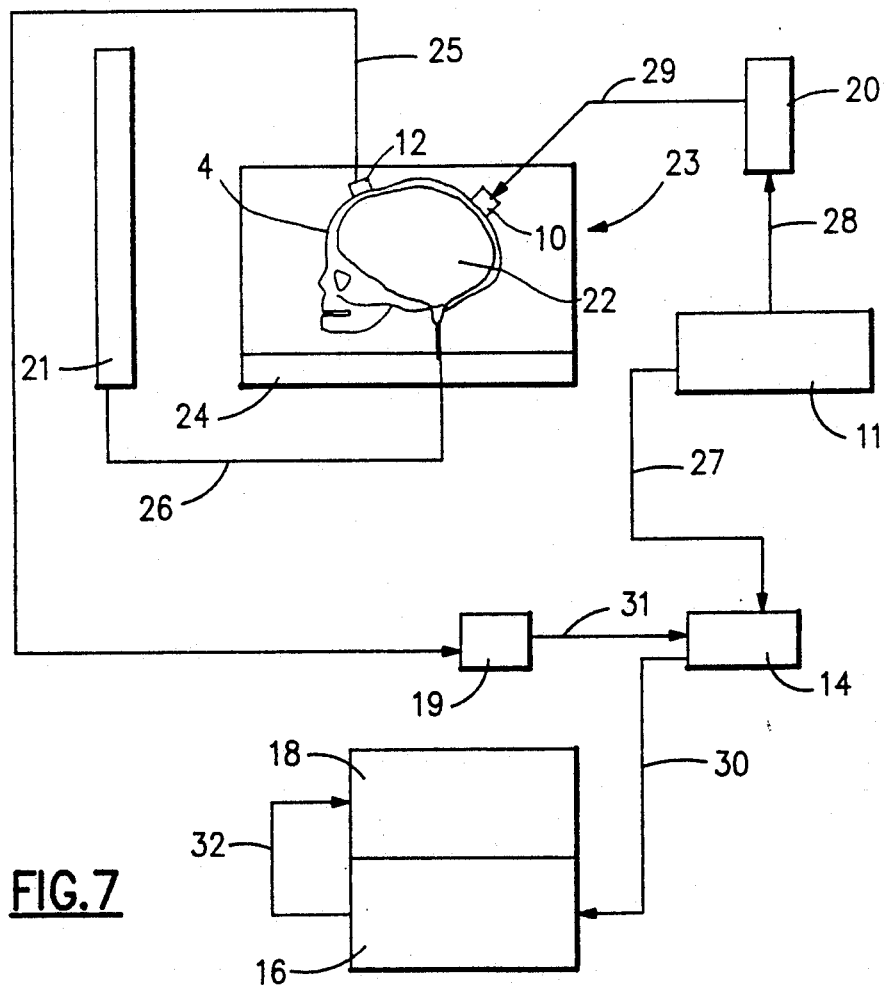
FIG. 7 is a block diagram of the laboratory setup used in Example 1.

Referring now to the included drawings, there is shown in FIGS. 1 and 7, an exciter transducer (10) which is preferably a Bruel and Kjaar Model 4810 vibration exciter. The exciting transducer (10) is preferably energized by a signal generator (11) such as a Bruel and Kjaar Model 1049 sine/noise generator. This input signal is also sent to a signal analyzer (14) which is preferably a spectrum analyzer, such as a Hewlett-Packard Model HP 3562A Low Frequency Spectrum Analyzer. The signal induced into a patient's skull (4) is transmitted as a wave along the skull to a sensing transducer (12) which is preferably a Bruel and Kjaar accelerometer Model 4384. The received signal is then fed to a signal analyzer (14). The analyzed signal is then sent to a digital computer (16) such as a 80386 IBM PC-compatible computer having a MATLAB TM program for further processing the signal to provide a resultant output which can be related to ICP by change from an established norm. The analyzed signal is displayed on a computer monitor (18) to give an indication of changes in ICP or to show frequency distribution which can be related to changes in ICP.

EXAMPLE I

Figure 2:
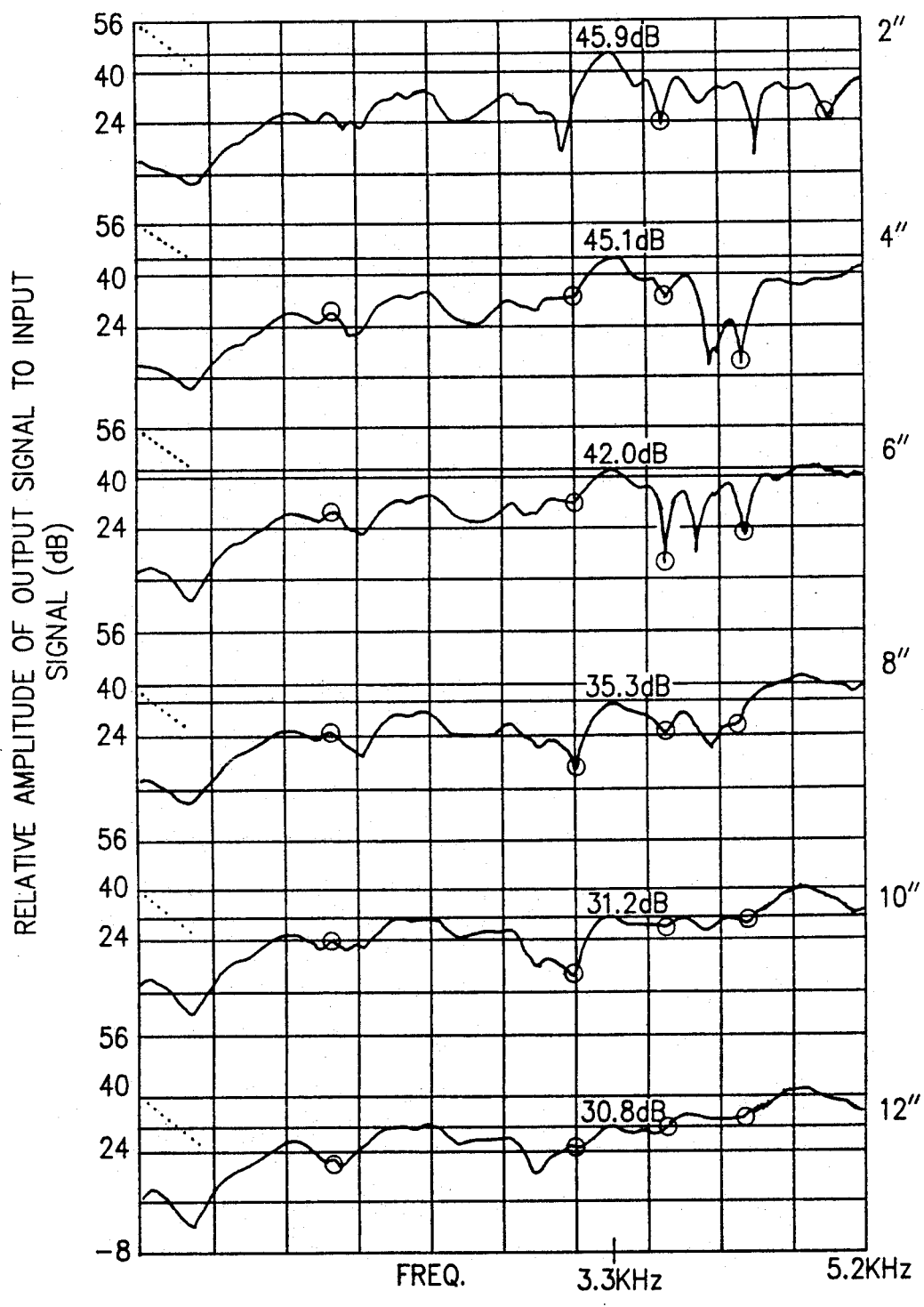
FIG. 2 is an actual reading of output gain (dB) from the analyzing apparatus plotted against output frequency components (Hz) at a series of different pressures; the skull's various frequency harmonics are readily discernible.
Figure 3:
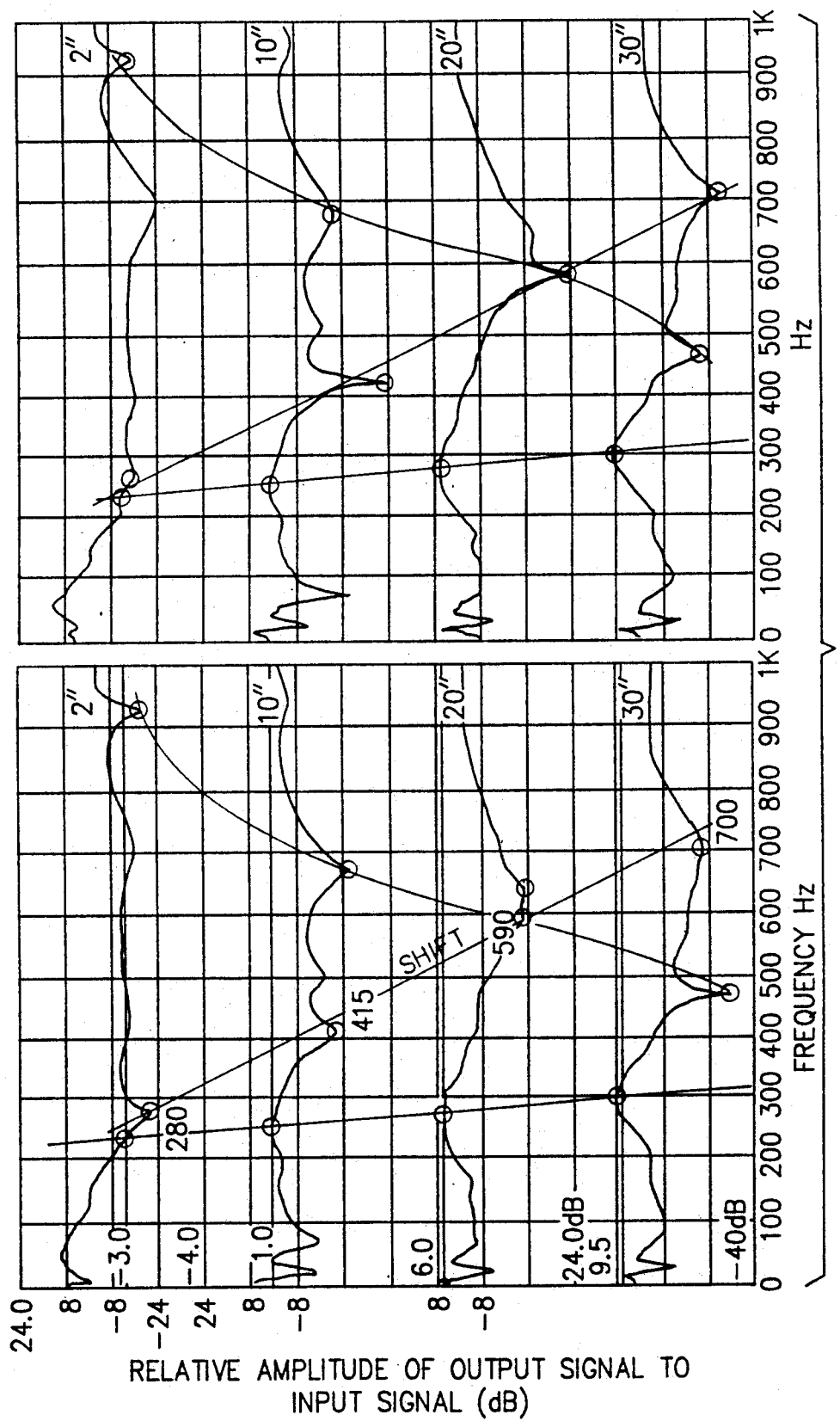
FIG. 3 is a series of charts of output gain (dB) versus output frequency components in another series of pressures and a different series of runs; shifts in the skull's frequency harmonics are shown over the various ICP's.
Figure 4:
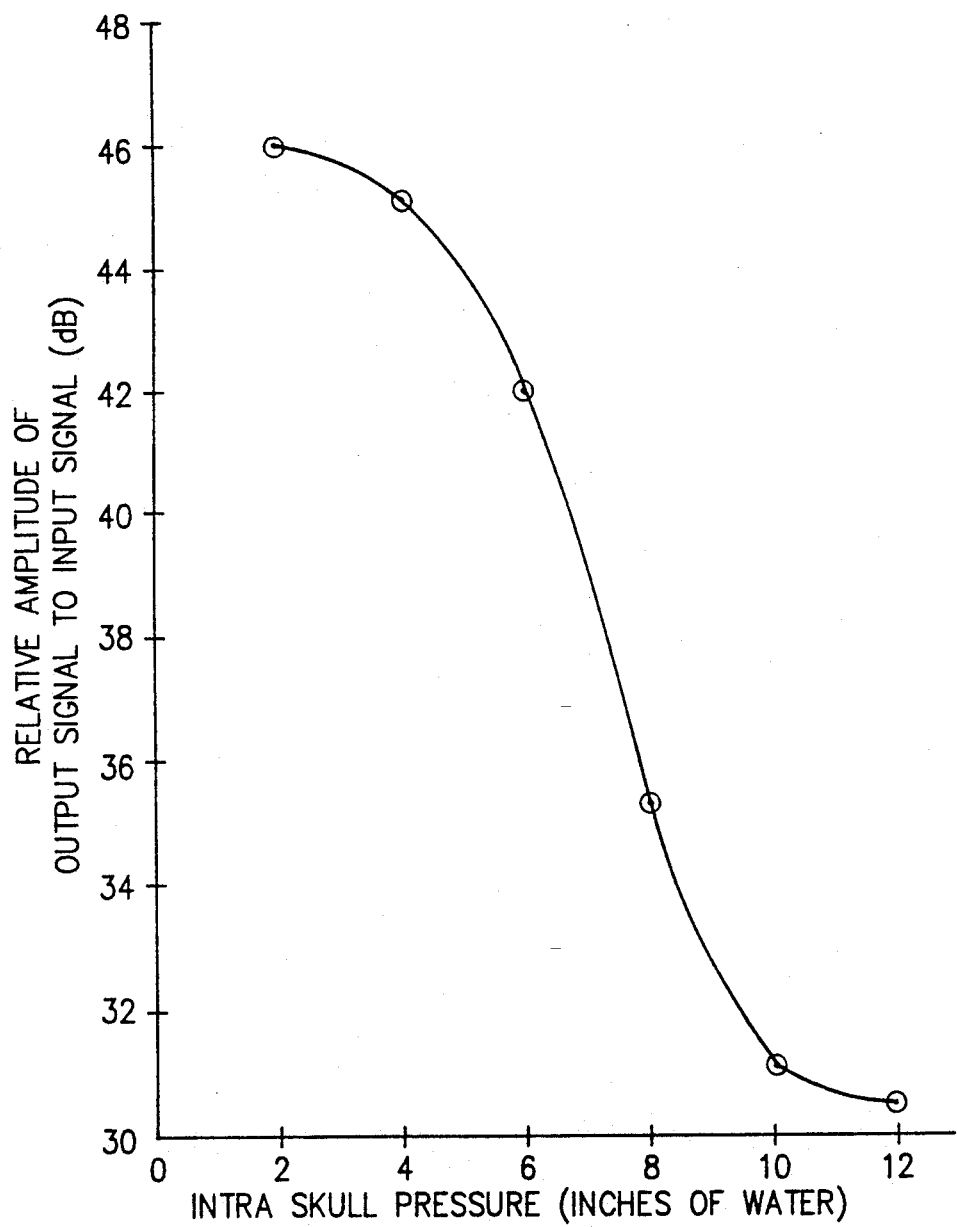
FIG. 4 is a plot of the FIG. 2 data showing a change in sensory output gain (dB) at 3.3 kHz as a function of intraskull pressure.
Figure 5:
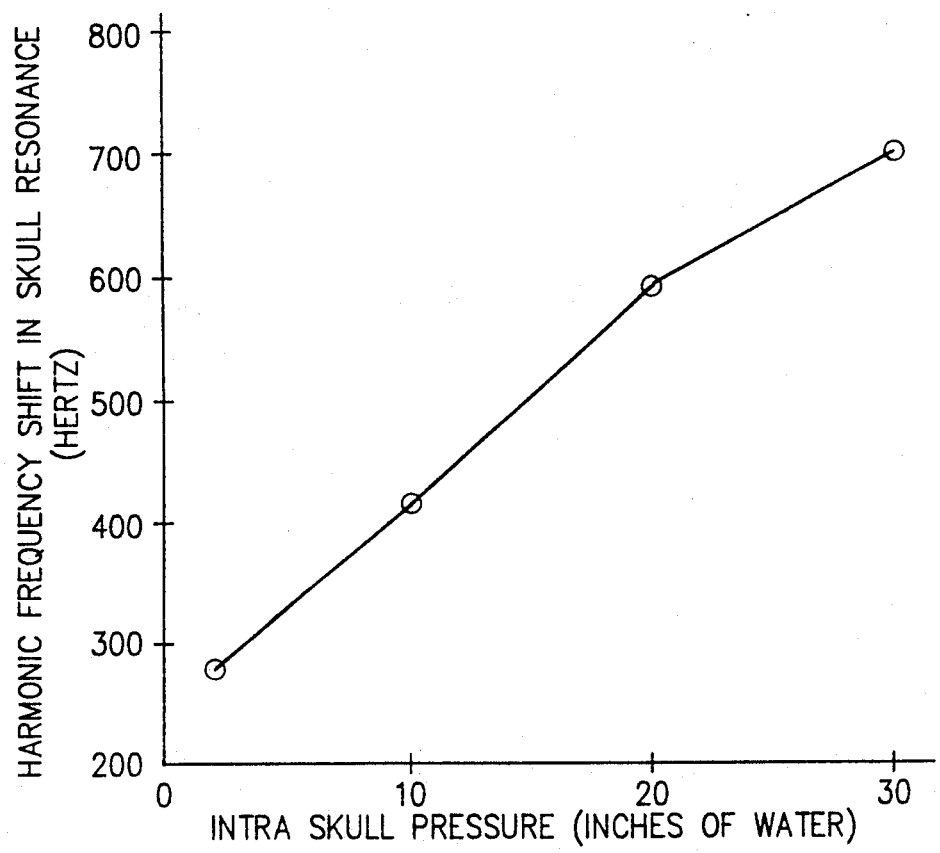
FIG. 5 is a plot of resonance frequency (Hz) versus ICP (mm $H_2O$); this plot clearly showing that resonance frequency shifts as a function of ICP.
Figure 6:
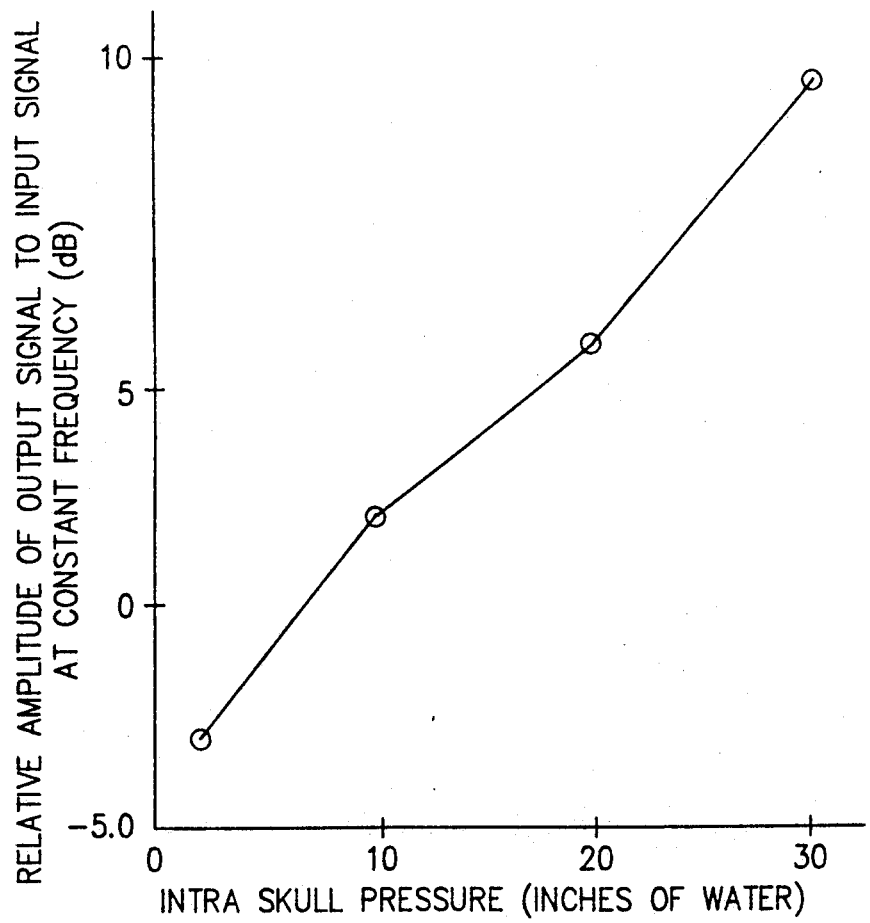
FIG. 6 is the sensory output gain (dB) in the 200 to 300 Hz range as a function of intraskull pressure.

In order to test the theoretical basis of the invention as discussed above, a skull (4) was employed which contained a bladder (22) into which water of a predetermined and controlled pressure could be injected from a water column (21) via a tube (26). The skull (4) was placed into a containment box (23) in which was placed a shock-absorbing cushion (24) to isolate the skull (4) from ambient background vibrations. The amount of water injected into the skull (4) was recorded for each run and ICP derived therefrom. A signal was induced in the skull by placing the transducer (10) in contact with the skull and activating the transducer (10) by setting the signal generator (11) in an autocorrelation mode and relaying this signal through a cable (28) to an amplifier which was set at a gain of 10 (20) and finally through another cable (29) to the transducer (10). The resultant vibratory wave induced in the skull (4) was received by the sensing transducer (12) and relayed via a cable (25) to an amplifier (19). This amplifier then relayed the signal through a cable (31) to the signal analyzer (14). The analyzer then performed computations on the input signal and the output signal and a signal indicative of these computations was then sent to a digital computer (16) through cable (30). Various algorithms were employed by the digital computer (16) to correlate the raw data and after being transmitted through a cable (32) to a screen (18) the correlated raw data was stored. The raw data obtained from the system is plotted in FIGS. 2 and 3 at various runs of different pressures. Additionally, the decibel output as a function of frequency for each of the number of pressures of the liquid within the skull (4) is plotted in FIGS. 2 and 3. Selected points on the various series of curves were then plotted in FIGS. 4, 5, and 6 to show a change in measured characteristic either intensity or harmonic frequency shift as a function of pressure, thus demonstrating the ability of the device to clearly correlate a change in a laboratory response of the simulated skull as a function of the liquid pressure within the skull.

While one preferred assembly of standard components has been described above numerous modifications thereof are possible.

What is claimed is:

1. A method of non-invasively measuring changes in a patient's intracranial pressure in said patient's skull from said patient's normal intracranial pressure, comprising the steps of:
   (a) measuring the thickness and radius of a patient's skull non-invasively by using non-invasive thickness measuring means;
   (b) generating a predetermined input vibration signal and applying said input signal at a first location on a patient's skull;
   (c) detecting an output vibration signal from a second location on said patient's skull, said output signal being a modification of said input signal, said input signal having been changed as a function of said patient's intracranial pressure as it travels from said first location to said second location;

(d) storing data characteristic of said thickness and radius, and said input and output signals into a data base; and (e) estimating said patient's normal intracranial pressure vibration signal from said data by using estimation means.

2. A method according to claim 1, wherein said data stored into said data base comprises natural frequency data.

3. A method according to claim 1, wherein said data stored into said data base comprises frequency response data.

4. A method according to claim 1, wherein said first location and said second location are located at substantially the same place on said patient's skull.

5. A method according to claim 1, wherein the estimation of frequency response at step e comprises the use of a microprocessor.

6. A method according to claim 1, wherein said input signal comprises a shock signal.

7. A system for non-invasively measuring changes in a patient's intracranial pressure from said patient's normal intracranial pressure, comprising:

(a) means for non-invasively measuring the thickness and radius of a patient's skull;

(b) means for generating a predetermined input vibration signal and applying said input signal at a first location on a patient's skull;

(c) means for detecting an output vibration signal from a second location on said patient's skull, said output signal being a modification of said input signal, said input signal having been changed as a function of said patient's intracranial pressure as it travels from said first location to said second location;

(d) means for storing data characteristic of said thickness and radius on said input and output signals into a first data base; and (e) means for estimating said patient's normal intracranial pressure vibration signal from said data by using estimation means.

8. A system according to claim 7, wherein the data stored by said data storing means comprise natural frequency data.

9. A system according to claim 7, wherein the data stored by said data storing means comprise frequency response data.

10. A system according to claim 7, wherein the means for generating and applying said input signal comprises an impact hammer.

11. A system according to claim 7, wherein the means for detecting said output signal comprises an accelerometer.

12. A system according to claim 7, wherein, the estimation means at step e, the calculating means at step f, and the comparison means at step h comprise a microprocessor.

13. A system according to claim 7, wherein the input signal comprises a shock.

14. A system according to claim 7, wherein the means for generating and applying said input signal, and the means for detecting said output signal comprise a vibration exciter transducer.

15. A system according to claim 7, wherein the means for detecting said output signal comprises a velocity sensor.

16. A system according to claim 7, wherein the means for detecting said output signal comprises a displacement sensor.

17. A system according to claim 7, wherein the means for measuring said skull's thickness comprises computer aided tomography means.

18. A system according to claim 7, wherein the data stored by said data storing means at step d comprises dynamic vibration behavior characteristics.

* * * * *

UNITED STATES PATENT AND TRADEMARK OFFICE
CERTIFICATE OF CORRECTION

PATENT NO. : 5,117,835
DATED : June 2, 1992
INVENTOR(S) : Edwin C. Mick

It is certified that error appears in the above-identified patent and that said Letters Patent is hereby corrected as shown below:

"Claim 7, col. 10, line 2, after "radius" delete "on" and insert --, and--".

Signed and Sealed this

Third Day of August, 1993

Attest:

MICHAEL K. KIRK

Attesting Officer

Acting Commissioner of Patents and Trademarks